US007582314B2

(12) United States Patent
Majeed et al.

(10) Patent No.: US 7,582,314 B2
(45) Date of Patent: Sep. 1, 2009

(54) COMPOSITIONS AND METHODS FOR THE MANAGEMENT OF HYPERPROLIFERATIVE DERMATOLOGICAL CONDITIONS

(75) Inventors: Muhammed Majeed, Piscataway, NJ (US); Subbalakshmi Prakash, Piscataway, NJ (US)

(73) Assignee: Sami Labs Ltd., Bangalore (IN)

( * ) Notice: Subject to any disclaimer, the term of this patent is extended or adjusted under 35 U.S.C. 154(b) by 77 days.

(21) Appl. No.: 10/710,778

(22) Filed: Aug. 2, 2004

(65) Prior Publication Data

US 2005/0123559 A1    Jun. 9, 2005

Related U.S. Application Data

(60) Provisional application No. 60/481,736, filed on Dec. 3, 2003.

(51) Int. Cl.
*A61K 36/324* (2006.01)
*A61K 36/00* (2006.01)

(52) U.S. Cl. ...................................................... 424/725
(58) Field of Classification Search ................... 424/725
See application file for complete search history.

(56) References Cited

U.S. PATENT DOCUMENTS

2002/0148478 A1* 10/2002 Pera ........................... 131/341

2002/0176900 A1* 11/2002 Yegorova ..................... 424/754

FOREIGN PATENT DOCUMENTS

| EP | 0552657 A1 * | 7/1992 |
| EP | 552657 A1 * | 1/1993 |
| WO | WO03080092 A1 * | 10/2003 |

OTHER PUBLICATIONS

Cummins et al. Cutaneous Malignant Melanoma; Mayo Clinic Proceedings, Rochester, Apr. 2006, vol. 81, Issue 4, p. 500, 8 pages (pp. 1-10 of ProQuest Direct).*
Balch et al. Prescription for Nutritional Healing, Second Edition; Avery Publishing, Garden City Park, New York, 1997, pp. 452-454.*

* cited by examiner

*Primary Examiner*—Patricia Leith
(74) *Attorney, Agent, or Firm*—Arent Fox LLP

(57) ABSTRACT

The invention describes compositions and methods for the management of hyperproliferative skin conditions such as psoriasis. The preferential composition contains a natural leukotriene inhibitor selected from *Boswellia serrata* gum resin, its extractives, isolates or derivatives in combination with a bioavailable organic selenium nutritional supplement. These compositions are administered orally and topically to the individual human or animal in need of treatment at optimal levels to manifest the desired benefits, with no untoward side effects

10 Claims, 4 Drawing Sheets

Improvement in psoriasis lesions –Patient 4, Patient 5, Patient 6.
Photographs show initial lesion and lesion appearance at 4 week intervals Patient 1:
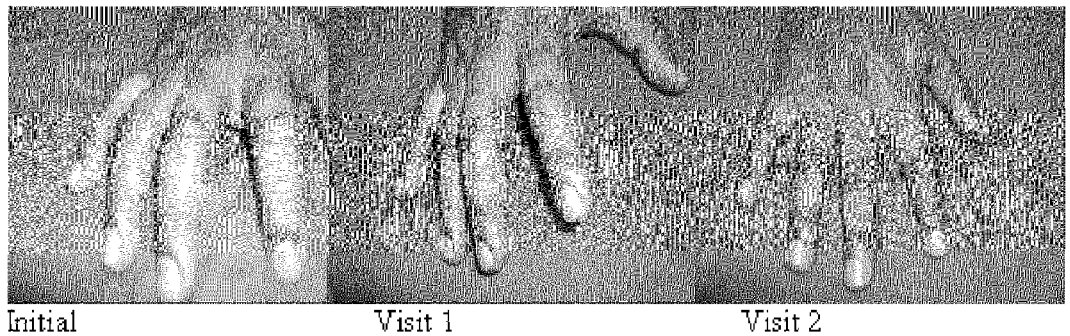
Initial  Visit 1  Visit 2
Patient 2:
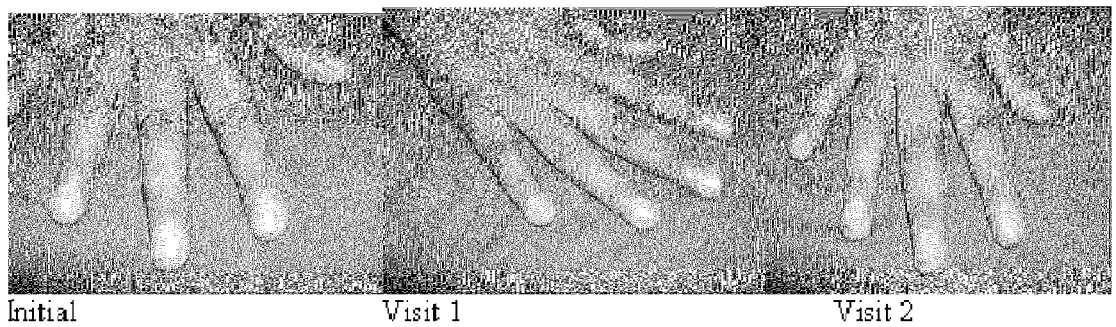
Initial  Visit 1  Visit 2
Patient 3
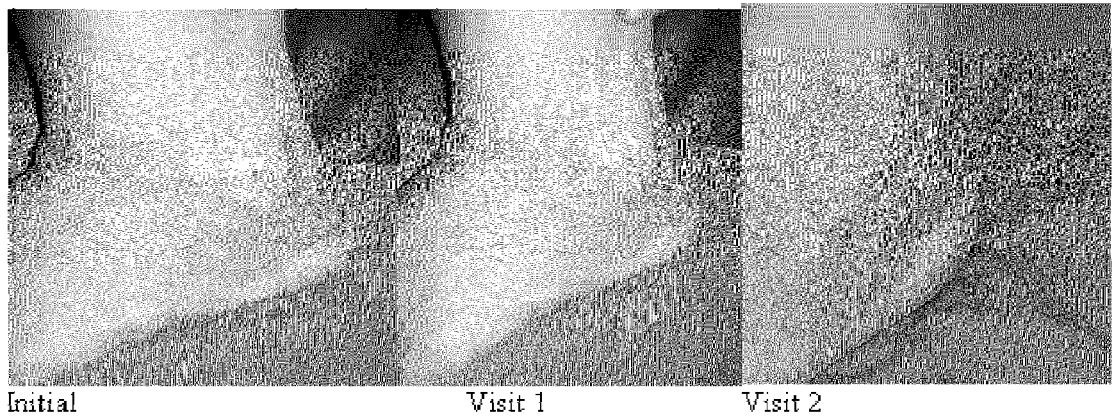
Initial  Visit 1  Visit 2
Figure 1: Improvement in psoriasis lesions –Patient 1, Patient 2, Patient 3.
Photographs show initial lesion and lesion appearance at 4 week intervals Patient 4
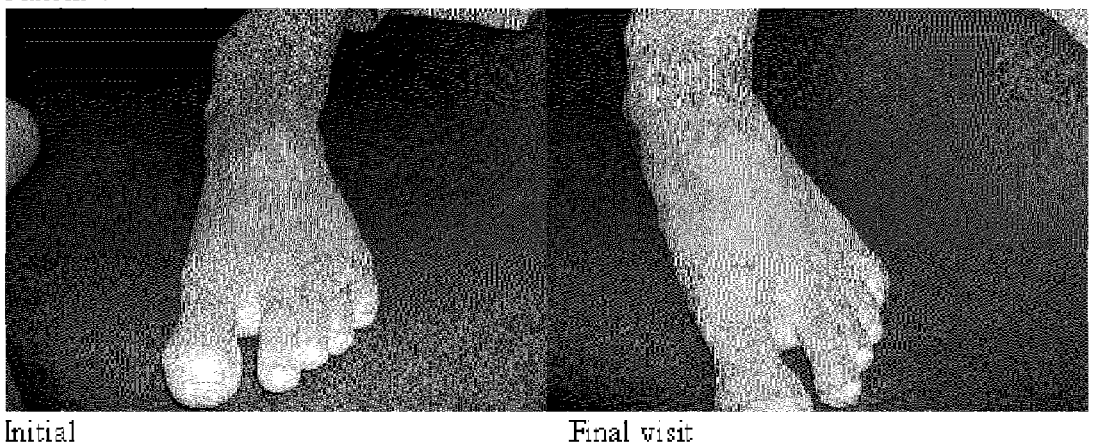
Initial　　　　　　　　　　　　Final visit
Patient 5
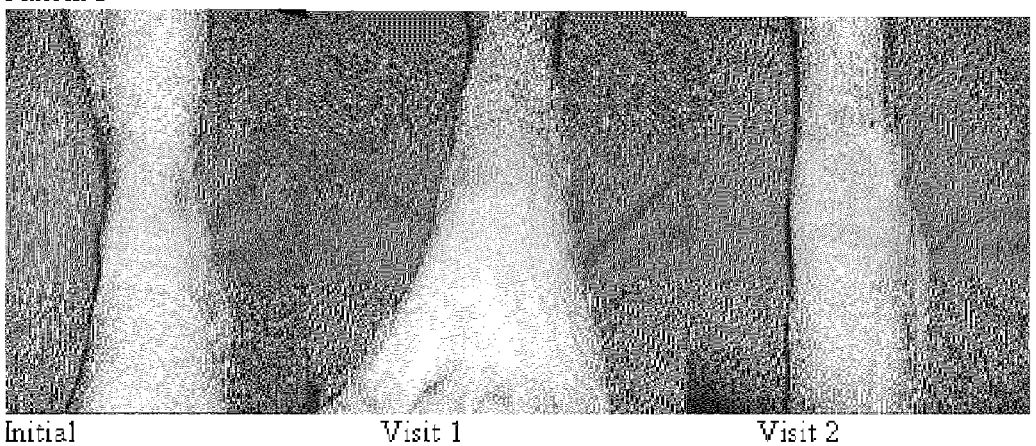
Initial　　　　　　　Visit 1　　　　　　　Visit 2
Patient 6
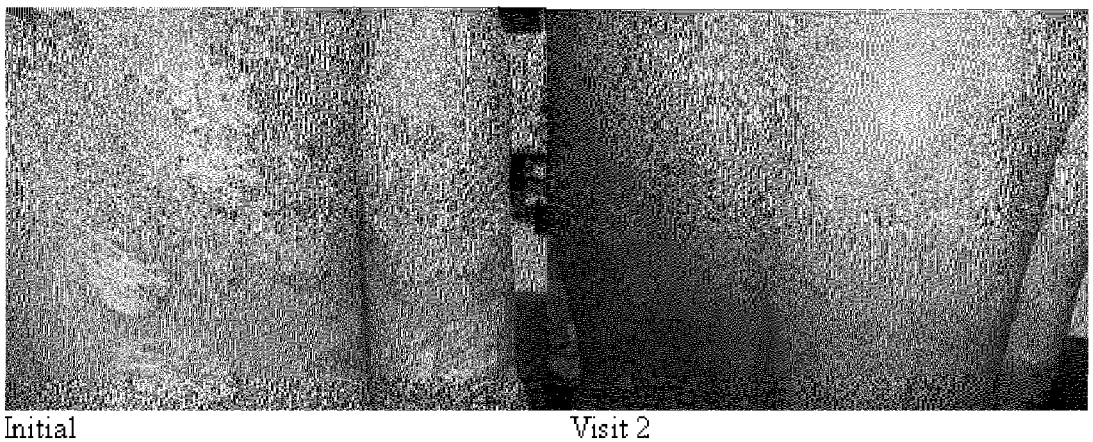
Initial　　　　　　　　　　　　Visit 2
Figure 2: Improvement in psoriasis lesions – Patient 4, Patient 5, Patient 6. Photographs show initial lesion and lesion appearance at 4 week intervals Patient 7
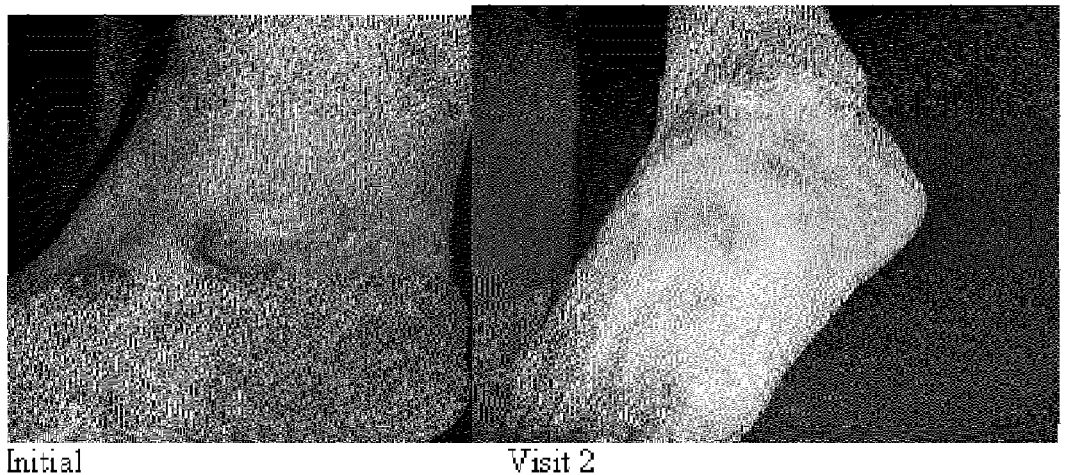
Initial                  Visit 2
Patient 8
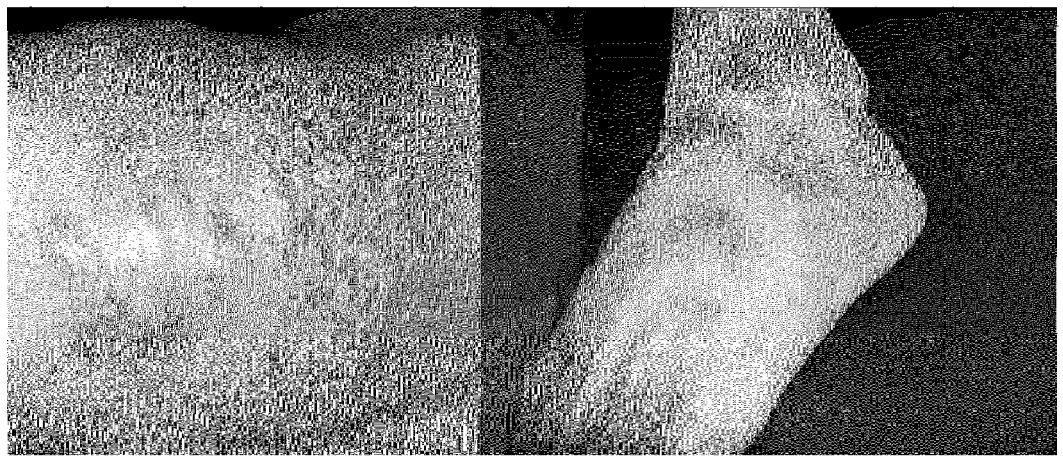
Initial                  Visit 2
Patient 9
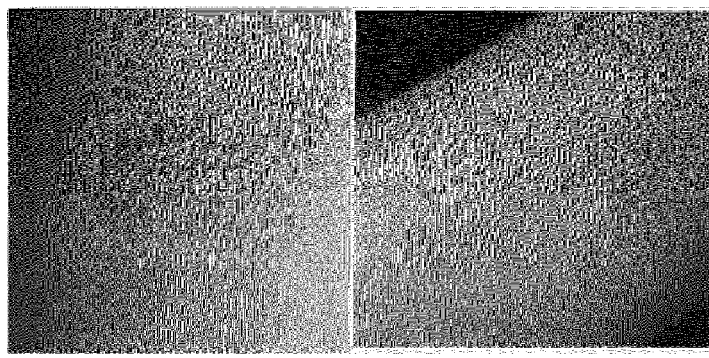
Initial                  Visit 2
Figure 3: Improvement in psoriasis lesions – Patient 7, Patient 8, Patient 9. Photographs show initial lesion and lesion appearance at 4 week intervals Patient 10
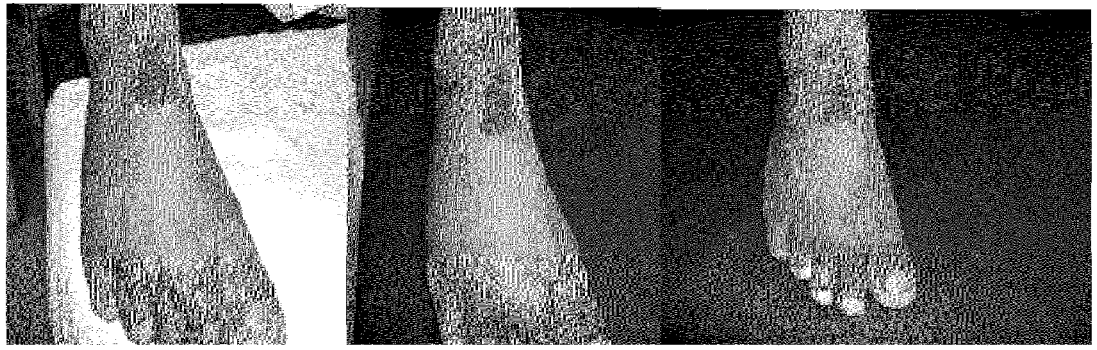
Patient 11
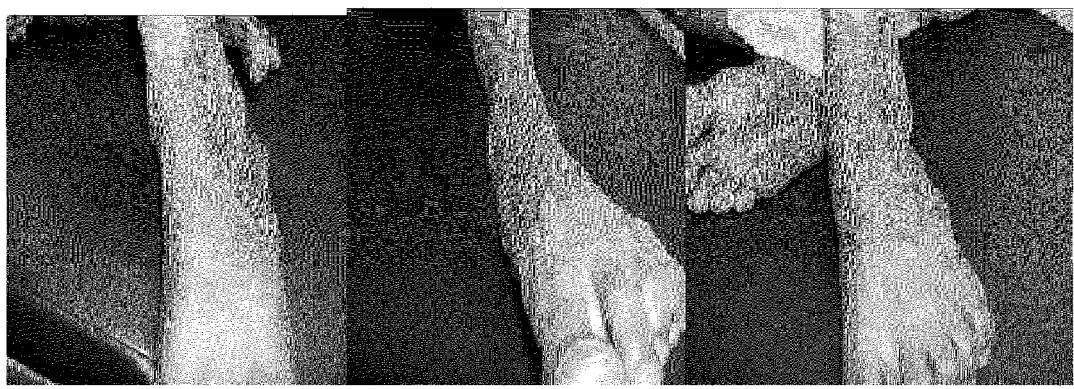
Initial  Visit 1  Visit 2
Patient 12
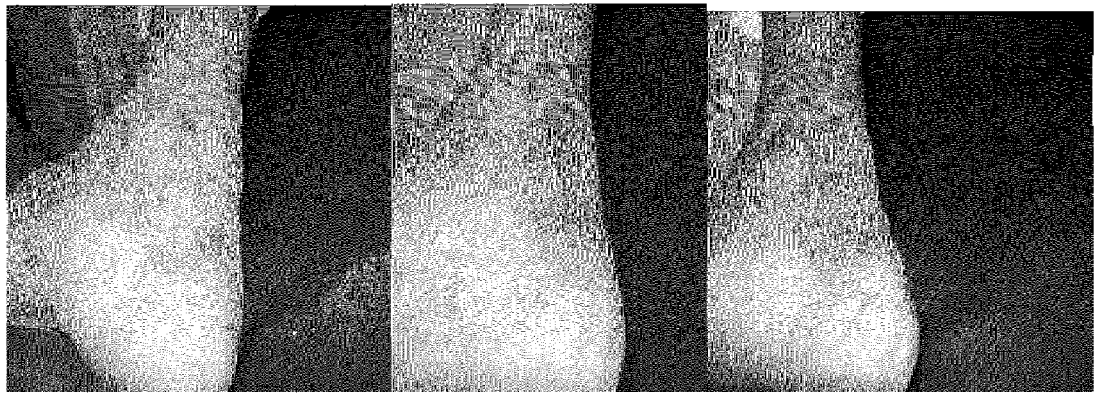
Initial  Visit 1  Visit 2
Figure 4: Improvement in psoriasis lesions –Patient 10, Patient 11, Patient 12.
Photographs show initial lesion and lesion appearance at 4 week intervals

COMPOSITIONS AND METHODS FOR THE MANAGEMENT OF HYPERPROLIFERATIVE DERMATOLOGICAL CONDITIONS

CROSS REFERENCE TO RELATED APPLICATIONS

This application claims the benefit of provisional U.S. Patent application No. 60/481,736 filed on Dec. 3, 2003, the disclosure of which is hereby incorporated by reference.

BACKGROUND OF INVENTION

1. Field of the Invention

The invention is related to compositions and methods for the management of hyperproliferative skin conditions such as psoriasis, and their associated symptoms. The compositions described herein contain a natural leukotriene inhibitor selected from Boswellia serrata gum resin, its extractives, isolates or derivatives in combination with a bioavailable organic selenium nutritional supplement. These compositions are administered orally and topically to the individual human or animal in need of treatment at optimal levels and in suitable dosage forms to manifest the desired benefits, with no untoward side effects.

2. Description of Prior Art

Psoriasis is a chronic skin disease marked by periodic flare-ups of sharply defined red patches covered by a silvery, flaky surface. In psoriasis the skin epidermis is subjected to destructive changes due to genetic abnormalities in the immune system that are triggered by stress and environmental factors. There is hyperproliferation of immature keratinocytes in the epidermis, forming patches or plaques with silvery, flaky dead skin shed from the surface. In the dermis, the blood vessels provide an increased blood supply to the abnormally multiplying keratinocytes, causing the underlying inflammation and redness characteristic of psoriasis. Several types of psoriasis exist occurring independently, concurrently or consequently. The most common form of psoriasis is plaque psoriasis. Psoriatic arthritis is a debilitating disorder that includes both psoriasis and arthritis.

Psoriasis is clinically addressed with topical medications, phototherapy, systemic medications. Agents such as steroidal drugs, cyclosporine, methotrexate, oral and topical retinoids, selenium sulfide used in pharmaceutical preparations for this purpose have various side effects. There is no known cure for psoriasis.

Boswellia serrata (Roxb.) Burseraceae is a large tree which grows in the dry and hilly parts of India. The exudate of Boswellia serrata is a gum resin commonly known as "Dhup", "Indian Frankincense" or "Indian Olibanum" (Anonymous, 1948 and Chopra et al, 1956), The gum resin known as Salai Guggal has been used in Ayurvedic system of medicine for the treatment of rheumatism, respiratory diseases and liver disorders (Kirtikar and Basu, 1935). Ancient Ayurvedic texts (Shushrutha Samhitha Gulabkunvarba, 1949) and Charaka Samhitha (Chowkhamba, 1968) mentioned the anti-rheumatic activity of guggals. The nonacidic oil fraction of gum resins of Boswellia was found to exhibit significant pain relieving effects in rats (Menon and Kar, 1971 and Menon and Kar, 1969). The acidic fraction of gum Boswellia serrata, containing boswellic acids, was found to exhibit antipyretic action in rats and rabbits (Singh and Atal, 1986, Singh et al., 1993). The acidic fraction of gum Boswellia serrata, however, was not known to have any analgesic property. In nature, boswellic acids occur in the gum or exudate from the tree Boswellia serrata (Roxb.). The gum contains a mixture of four boswellic acids.

Boswellic acids inhibit 5-lipoxygenase (Safayhi et al., 1992) the enzyme which catalyzes conversion of arachidonic acid to inflammatory leukotrienes. Boswellic acids also inhibit the enzyme human leukocyte elastase (HLE) which catalyzes connective tissue break down (Safayhi et al., 1997).

Inflammatory leukotrienes have been implicated in the pathogenesis and pathophysiology of psoriasis. In lesional skin from psoriasis and eczema patients, leukotriene B4 was found to increase by approximately 6.6-fold (Reilly et al. 2000). A 5-lipoxygenase catalyzed product from arachidonic acid, leukotriene B4, is considered to play a significant role in the pathogenesis of psoriasis (Iversen et al., 1997). A massive increase in human leukocyte elastase (HLE) activity was found in lesional skin of psoriasis (31 times), allergic contact dermatitis (55 times), and atopic dermatitis (35 times), but not in uninvolved skin of diseased patients (Wiedow, 1992).

WO 96/19212 describes the use of boswellic acids in treating brain tumors.

WO 97/07796 describes the use of boswellic acid and its derivatives for inhibiting normal and increased leukocytic elastase or plasmin activity.

U.S. Pat. No. 5,888,514 describes a natural composition containing boswellic acids for treating bone or joint inflammation.

U.S. Pat. No. 5,629,351 describes a boswellic acid composition and the preparation thereof.

U.S. Pat. No. 5,494,668 describes a boswellic acid composition for treating musculoskeletal disorders.

U.S. Pat. No. 5,720,975 describes the use of incense for treating Alzheimer's disease.

EP 0552657 describes the use of pure boswellic acid, a physiologically acceptable salt, derivative, or a salt of the derivative or a boswellic acid containing herbal preparation for the prophylaxis and/or control of inflammatory processes caused by increased leukotriene formation in human and veterinary medicine.

WO 00/57893 describes compositions containing Boswellia serrata extract wherein Boswellia serrata extract, boswellic acid or a derivative thereof is useful in preparing skin care or hair care compositions with the ability to provide a soothing effect to irritated skin.

Selenium is a vital trace element nutrient with multiple roles in the growth and functioning of living cells in higher animals and humans. At the molecular level, selenium (as selenocysteine) is an essential component of the active sites of the antioxidant enzyme glutathione peroxidase, and the enzymes participating in thyroid functions iodothyronine-5'-deiodinase and mammalian thioredoxin reductase. Selenium is also present in several other mammalian selenoproteins. Low selenium status has been linked with the occurrence of decreased immunity to diseases and the prevalence of various forms of cancer.

Patients with moderate or severe psoriasis have been shown to have low blood selenium levels and increased levels of malondialdehyde, a product of free radical induced oxidation (Corrocher, et al. 1989). Low selenium dietary intake has been linked to the progression of psoriasis in a clinical study (Serwin, et al. 1999). It has been demonstrated in both human subjects and experimental animals that topical selenomethionine reduces the degree of damage to the skin induced by UV radiation (Burke, et al., 1992). The antioxidant action of selenomethionine through its role in the antioxidant enzymes (Cronin, 2000) may therefore help in cases of psoriasis.

Recent studies suggest that that psoriasis is not primarily a skin disorder but an immunological disturbance under the skin. The skin manifestations are a result of overstimulation of superficial skin cells (Langerhans cells) due to increased production of interleukin 2, 6 and 8 as well the diminished production of transforming growth-factor-alpha Interleukin-10 (Christ, 1999).

The effect of Selenium supplementation (400 micrograms/day for 6 weeks as Se-yeast, containing about 70% selenomethionine) on skin and blood Se-content, on skin glutathione peroxidase activity and on various chemical and immunological parameters of blood and skin was investigated in 7 psoriatic patients. The results of this study suggested that selenomethionine may be able to modulate the immunological mechanism of psoriatic lesions by increasing the number of CD4+ T cells (Harvima, 1993).

Tumor necrosis factor-alpha (TNF-alpha) and its receptors play important roles in the induction and maintenance of psoriatic lesions. A recent study reports that oral supplementation with selenomethionine was ineffective as adjuvant treatment in plaque psoriasis and may contribute to the maintenance of elevated TNF-R1 (soluble TNF-alpha receptor type 1) concentration in psoriasis patients despite the remission of skin lesions. (Serwin et al., 2003).

Patent application CN1233482 describes the application of glossy selenium enriched ganoderma in the treatment of psoriasis.

WO02096429 describes an agent for the external therapy of psoriasis in the form of liposomal emulsions of preparations of methylxathine group, selenium and some other preparations are used as active substances.

IT1244459 describes Pharmaceutical compositions which can be administered topically for the treatment of skin diseases such as vitiligo, acne, psoriasis, alopecia, hypotrichosis, comprising one or more oils of animal origin selected from cod liver oil, mink oil and tortoise oil containing lithium, zinc, copper and possibly gold, silver, sulphur, selenium and silicon dissolved or dispersed in them are described.

U.S. Pat. No. 6,630,442 describes a composition of glutathione and selenium, as a selenoamino acid or selenium yeast extract and an epidermal growth factor in a topical carrier and method of using the composition to reduce and repair skin damage, resulting from aesthetic (exfoliation and chemical peels) and surgical (laser and other therapies) procedures and other chemical and thermal burns to the cutaneous tissues.

None of the prior art cited above addresses psoriasis with a natural dual inhibitor of 5-lipoxygenase and human leukocyte elastase in combination with organic selenium supplement. The anti-complementary activity of boswellic acids is detailed in literature (Kapil, A et al. 1992). The complement-dependent induction of TNF-alpha is a well-established pathway. Therefore the combination treatment of the current invention would prevent any potential elevation of TNF-alpha levels not addressed by selenium supplementation.

The following is a list of literature cited in this application, each of which is hereby incorporated by reference in its entirety:

Anonymous (1948), The Wealth of India: Raw Materials, Vol I, CSIR Publications, Delhi, pp 208-210.

Chopra, R. N. Nayar, S. L., Chopra, I. C. (1956), Glossary of India Medicinal Plants, SCIR, Delhi.Chowkhamba (1968), Charaka Samhita ($2^{nd}$ ed), Sanskrit Series Office, Varanasi.

Kirtikar, K. R. and Basu, B. D. (1935), Indian Medicinal Plants, Vol. I, pp. 521- 529.

Menon, M. K. and Kar. A. (1971), Analgesic and psychopharmacological effects of the gum resin of *Boswellia serata*. Planta Med. 19:338-341.

Menon, M. K. and Kar, A. (1969). Analgesic effects of the gum resin of *Boswellia serrata*. Life Sciences 8(1):1023-28.

Singh, G. B. and Atal, C. K. (1986), Pharmacology of an extract of salai guggal ex-*Boswellia serrata*, a new nonsteroidal anti-inflammatory agent, Agents and Actions 18 (3/4): 407-411.

Singh, G. B. et al. (1993), Boswellic Acids, Drugs of the Future 18(4):307 309.

Sushruta Samhita (1949), Shree Gulabkunvarba, Vol 1 6, Ayurvedic Soc., Jamnagar.

Reilly D M. et al. (2000) Inflammatory mediators in normal, sensitive and diseased skin types. Acta Derm Venereol 80(3):171-4.

Iversen L, et al. (1997) Significance of leukotriene-A4 hydrolase in the pathogenesis of psoriasis. Skin Pharmacol. 10(4):169-77.

Wiedow O, et al. (1992) Lesional elastase activity in psoriasis, contact dermatitis, and atopic dermatitis. Invest Dermatol. 99(3):306-9.

Safayhi, H. et al. (1992) Boswellic acids: novel, specific, non-redox inhibitors of 5-lipoxygenase. J. Pharmacol. Exp. Ther. 261:1143-6.

Safayhi, H. et al. (1997) Inhibition by boswellic acids of human leukocyte elastase. J. Pharmacol. Exp. Ther. 281:460-463.

Corrocher, R. et al. (1989) Effect of fish oil supplementation on erythrocyte lipid pattern, malondialdehyde production and glutathione-peroxidase activity in psoriasis. Clin Chim Acta 179(2):121-31.

Serwin A B, et al. (1999) Selenium nutritional status and the course of psoriasis. Pol Merkuriusz Lek. 6(35):263-5.

Burke, K. E. et al. (1992) The effect of topical L-selenomethionine on minimal erythema dose of ultraviolet irradiation in humans. Photodermatol Photoimmunol Photomed. 9(2): 52-7.

Cronin, J. R. (2000) Dietary selenium: Elemental Nutrition for Muscles, Immunity, Well-Being and Cancer Prevention. Alt. Complement. Therap. 6(6):342-346.

Christ H W. (1999) Immunomodulating therapy of psoriasis vulgaris. Med Klin 94 Suppl 3:90-2.

Serwin, A. B. et al. Soluble tumor necrosis factor-alpha receptor type 1 during selenium supplementation in psoriasis patients. Nutrition. October 2003; 19(10):847-850.

Harvima, R. J. (1993) Screening of effects of selenomethionine-enriched yeast supplementation on various immunological and chemical parameters of skin and blood in psoriatic patients. Acta Derm. Venerol. 73(2): 88-91.

Kapil, A and Moza, N Anticomplementary activity of boswellic acids—an inhibitor of C3-convertase of the classical complement pathway. Int J Immunopharmacol. 1992 October; 14(7):1139-43.

SUMMARY OF INVENTION

The invention describes compositions and methods for the management of hyperproliferative skin conditions such as psoriasis, and their associated symptoms. The compositions described herein contain a natural leukotriene inhibitor selected from *Boswellia serrata* gum resin, its extractives, isolates or derivatives in combination with a bioavailable organic selenium nutritional supplement. These compositions are administered orally and topically to the individual human or animal in need of treatment at optimal levels to manifest the desired benefits, with no untoward side effects.

BRIEF DESCRIPTION OF DRAWINGS

FIG. 1 shows the appearance of psoriatic lesions in patient 1, patient 2, patient 3 initially, at the end of week 8 (visit 1) and the end of week 12 (visit 2) during treatment.

FIG. 2 shows the appearance of psoriatic lesions in patient 4, patient 5, patient 6 initially, at the end of week 8 (visit 1) and the end of week 12 (visit 2) during treatment.

FIG. 3 shows the appearance of psoriatic lesions in patient 7, patient 8, patient 9 initially, at the end of week 8 (visit 1) and the end of week 12 (visit 2) during treatment.

FIG. 4 shows the appearance of psoriatic lesions in patient 10, patient 11, patient 12 initially, at the end of week 8 (visit 1) and the end of week 12 (visit 2) during treatment.

DETAILED DESCRIPTION

Hyperproliferative skin disorders are exemplified by psoriasis. Psoriasis is a chronic skin disease characterized by periodic flare-ups in the form of red patches covered by a silvery, flaky surface that appear on the skin. It is attributed to genetic abnormalities in the immune system that are triggered by environmental factors, and therefore classified as an autoimmune disorder. There are several variants of psoriasis of which plaque psoriasis is the most common and is seen on the elbows, knees and lower back. In psoriatic arthritis, psoriatic lesions are accompanied by symptoms of arthritis. Psoriatic arthritis is characterized by stiff, tender, and inflamed joints.

The current invention addresses hyperproliferative skin conditions with a novel treatment regimen in which a natural dual acting inhibitor of 5-lipoxygenase and human leukocyte elastase is ingested orally, as well as applied topically, in combination with a bioavailable organic selenium supplement which is ingested orally.

The processes leading to all autoimmune disease involve the human leukocyte antigen (HLA) system, which is genetically regulated. Malfunction of this system is at the root of most immune disorders, including psoriatic arthritis. The current invention is directed towards supplying nutrients that would potentially inhibit the inflammatory process through inhibiting the expression of pro-inflammatory enzymes and modulating the expression of keratinocyte growth factor. Successful treatment entails configuring the correct dosing regimen that would favorably influence the underlying genetic processes involved.

Exemplary embodiments of the current invention present compositions and dosing regimens to effect successful treatment of psoriasis.

EXAMPLE 1

Compositions of the Invention

An exemplary embodiment of the active ingredient composition of the oral formulation of the invention is presented in Table 1

TABLE 1

| Active Ingredient Composition of the Oral dosage form | |
| --- | --- |
| Active ingredient | Quantity |
| Beta-boswellic acid | 64 mg |
| Acetyl-beta-boswellic acid | 48 mg |
| 11-keto-beta-boswellic acid | 24 mg |
| Acetyl-11-keto-beta-boswellic acid | 32 mg |

TABLE 1-continued

| Active Ingredient Composition of the Oral dosage form | |
| --- | --- |
| Active ingredient | Quantity |
| L(+)-Selenom ethionine (trituration in Dicalcium phosphate) | 20 mg |

The formulation is prepared in the form of a capsule, tablet, power, spansule or other dosage form for oral administration, with commonly used excipients and additives for such purposes.

An exemplary embodiment of the formulation for topical application is presented in Table 2.

TABLE 2

| Composition of the topical cream | |
| --- | --- |
| Ingredient | % (w/w) |
| Purified water | 60.000 |
| Carbomer 940 | 0.250 |
| Glycerin | 4.000 |
| Methylparaben | 0.200 |
| Edetate sodium | 0.010 |
| Cetyl alcohol | 3.500 |
| Stearyl alcohol | 3.500 |
| Stearic acid | 6.500 |
| Glyceryl stearate | 2.500 |
| PEG-100 stearate | 2.500 |
| Isopropyl palmitate | 6.000 |
| Vitamin E acetate | 1.000 |
| Dimethicone | 0.100 |
| Propylparaben | 0.100 |
| Vitamin A Palmitate | 0.100 |
| Ascorbyl palmitate | 0.200 |
| BOSWELLIN | 5.000 |
| Purified water | 2.000 |
| Triethanolamine | 0.400 |
| Imiduria | 0.300 |

BOSWELLIN (a trademark of Sabinsa Corporation, NJ, USA) is a standardized *Boswellia serrata* gum resin extract containing beta-boswellic acid, acetyl-beta-boswellic acid, 11-keto-beta-boswellic acid and Acetyl-11-keto-beta-boswellic acid.

The active ingredient may be formulated as a cream, lotion, patch, gel or any other topical dosage form.

EXAMPLE 2

Treatment of Psoriatic Human Subjects with the Composition and Method of the Invention 12 patients (6 males and 1 female) 18-65 years of age, presenting with primary plaque and secondary scale manifested as annular, polycyclic, morbiliform lesions accompanied by Itching, peeling of skin, and bleeding on scratching, participated in the study.

The patients was administered tablets containing 400 mg boswellic acids and 100 mcg of selenium in the form of L(+)-Selenomethionine orally and also treated with a topical cream containing 400 mg of boswellic acids.

The daily dose regimen followed was 1 tablet as above with topical application as above, thrice daily for 150 days. PASI score (Psoriasis Area Severity Index) which takes into account body surface area as well as erythema (redness), induration (thickness), and scaliness, was assessed at 4 week intervals. Serum biochemical parameters were similarly assessed.

Psoriasis affected parts of the body were photographed at the initiation of the study and at 4 week intervals The patients were followed up for another 30 days and showed improvement in symptoms of psoriasis with no untoward side effects.

The effects of the treatment on the external manifestations of psoriasis are photographically represented in FIGS. 1-4.

The invention claimed is:

1. A method of treating psoriasis affected area of the skin, scalp or nails comprising the steps of:
   a) orally administering to a psoriasis affected individual a composition comprising 400 mg boswellic acids, 100 micrograms of elemental selenium, and a pharmaceutically acceptable carrier, three times per day; and
   b) topically applying to the affected area a composition comprising 5% w/w *Boswellia serrata* gum resin extract comprising beta-boswellic acid, acetyl-beta-boswellic acid, 11-keto-beta-boswellic acid, and acetyl-11-keto-beta-boswellic acid, and a pharmaceutically acceptable carrier three times per day.

2. The method of claim 1, wherein the elemental selenium is in the form of selenomethionine.

3. A method of treating psoriasis affected area of the skin, scalp or nails comprising the steps of:
   a) orally administering to a psoriasis affected individual a composition comprising 400 mg boswellic acids, 100 micrograms of elemental selenium in the form of selenomethionine, and a pharmaceutically acceptable carrier, three times per day; and
   b) topically applying to the affected area a composition comprising 5% w/w *Boswellia serrata* gum resin extract comprising beta-boswellic acid, acetyl-beta-boswellic acid, 11-keto-beta-boswellic acid, and acetyl-11-keto-beta-boswellic acid, and a pharmaceutically acceptable carrier three times per day.

4. A method of treating psoriasis affected area of the skin, scalp or nails comprising the steps of:
   a) orally administering to a psoriasis affected individual a composition comprising 400 mg boswellic acids, 100 micrograms of elemental selenium in the form of high selenium yeast, and a pharmaceutically acceptable carrier, three times per day; and
   b) topically applying to the affected area a composition comprising 5% w/w *Boswellia serrata* gum resin extract comprising beta-boswellic acid, acetyl-beta-boswellic acid, 11-keto-beta-boswellic acid, and acetyl-11-keto-beta-boswellic acid, and a pharmaceutically acceptable carrier three times per day.

5. A method of treating psoriasis affected area of the skin, scalp or nails comprising the steps of:
   a) orally administering to a psoriasis affected individual a composition comprising 400 mg boswellic acids, 100 micrograms of selenomethionine, and a pharmaceutically acceptable carrier three times per day; and
   b) topically applying to the affected area a composition comprising 5% w/w *Boswellia serrata* gum resin extract comprising beta-boswellic acid, acetyl-beta-boswellic acid, 11-keto-beta-boswellic acid, and acetyl-11-keto-beta-boswellic acid, and a pharmaceutically acceptable carrier three times per day.

6. The method of claim 5, wherein the 400 mg of boswellic acids of the orally administered composition comprises beta-boswellic acid, acetyl-beta-boswellic acid, 11-keto-beta-boswellic acid and acetyl-11-keto-beta-boswellic acid.

7. The method of claim 5, wherein the 5% w/w *Boswellia seratta* gum resin extract comprises 400 mg boswellic acids comprising a mixture of beta-boswellic acid, acetyl-beta-boswellic acid, 11-keto-beta-boswellic acid and acetyl-11-keto-beta-boswellic acid.

8. The method of claim 5, wherein the orally administered composition contains 400 mg of acetyl-11-keto-beta-boswellic acid.

9. The method of claim 5, wherein the Selenomethionine is L(+)-Selenomethionine.

10. The method of claim 5, wherein the total daily topical dose of boswellic acids is 1200 mg, administered in a plurality of individual doses.

* * * * *